(12) United States Patent
Varghese et al.

(10) Patent No.: US 7,166,075 B2
(45) Date of Patent: Jan. 23, 2007

(54) ELASTOGRAPHIC IMAGING OF IN VIVO SOFT TISSUE

(75) Inventors: Tomy Varghese, Madison, WI (US); James A. Zagzebski, Madison, WI (US); Udomchai Techavipoo, Madison, WI (US); Quan Chen, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 543 days.

(21) Appl. No.: 10/094,844

(22) Filed: Mar. 8, 2002

(65) Prior Publication Data

US 2003/0171672 A1  Sep. 11, 2003

(51) Int. Cl.
*A61B 8/00* (2006.01)

(52) U.S. Cl. .................. 600/439; 600/407; 600/437; 600/442; 600/446; 600/462; 600/463; 600/466; 606/27; 606/28; 606/29; 606/30; 606/31; 606/41; 601/2; 601/3; 601/4

(58) Field of Classification Search .............. 606/1, 606/27–31, 41, 32; 600/437, 442, 446, 466, 600/407, 443, 467, 587, 429, 439, 462, 463; 324/307, 309; 601/2
See application file for complete search history.

(56) References Cited

U.S. PATENT DOCUMENTS 5,107,837 A    4/1992  Ophir et al.
5,178,147 A *  1/1993  Ophir et al. ............... 600/437
5,265,612 A * 11/1993  Sarvazyan et al. .......... 600/471
5,293,870 A    3/1994  Ophir et al.
5,524,636 A *  6/1996  Sarvazyan et al. .......... 600/587
5,848,969 A * 12/1998  Panescu et al. ............ 600/462
5,919,139 A *  7/1999  Lin ........................... 600/443
6,241,725 B1*  6/2001  Cosman ...................... 606/41
6,277,074 B1*  8/2001  Chaturvedi et al. ........ 600/437
6,488,626 B1* 12/2002  Lizzi et al. ................ 600/437
6,514,204 B1*  2/2003  Alam et al. ................ 600/442
6,575,969 B1*  6/2003  Rittman et al. ............. 606/41
6,626,855 B1*  9/2003  Weng et al. .................. 601/3
2002/0068870 A1*  6/2002  Alam et al. ................ 600/446

(Continued)

FOREIGN PATENT DOCUMENTS

EP    0 920 833 A1    6/1999

(Continued)

OTHER PUBLICATIONS

F. Kallel, et al., "The Feasibility of Elastographic Visualization of HIFU-Induced Thermal Lesions in Soft Tissues," Ultrasound in Med. & Biol. 25(4):641-647, 1999.

(Continued)

*Primary Examiner*—Brian L. Casler
*Assistant Examiner*—Baisakhi Roy
(74) *Attorney, Agent, or Firm*—Boyle Fredrickson Newholm Stein & Gratz S.C.

(57) ABSTRACT

Elastographic images provide visualization in two or three dimensions of RF ablation lesions to guide in the ablation process. Compression may be applied using the RF probe. A similar technique may be applied to in vivo imaging of soft tissue without ablation.

23 Claims, 3 Drawing Sheets

U.S. PATENT DOCUMENTS

2003/0065267 A1 * 4/2003 Smith .................. 600/466

FOREIGN PATENT DOCUMENTS

WO     WO 01/06927 A1    2/2001

OTHER PUBLICATIONS

J. Ophir, et al., "Elastography: A Quantitative Method for Imaging the Elasticity of Biological Tissues," Ultrasonic Imaging 13:111-134, 1991.

R. Righetti, et al., "Elastographic Characterization of HIFU-Induced Lesions in Canine Livers," Ultrasound in Med. & Biol. 25(7):1099-1113, 1999.

R.J. Stafford, et al., "Elastographic Imaging of Thermal Lesions in Soft Tissue: A Preliminary Study *In Vitro*," Ultrasound in Med. & Biol. 24(9):1449-1458, 1998.

* cited by examiner

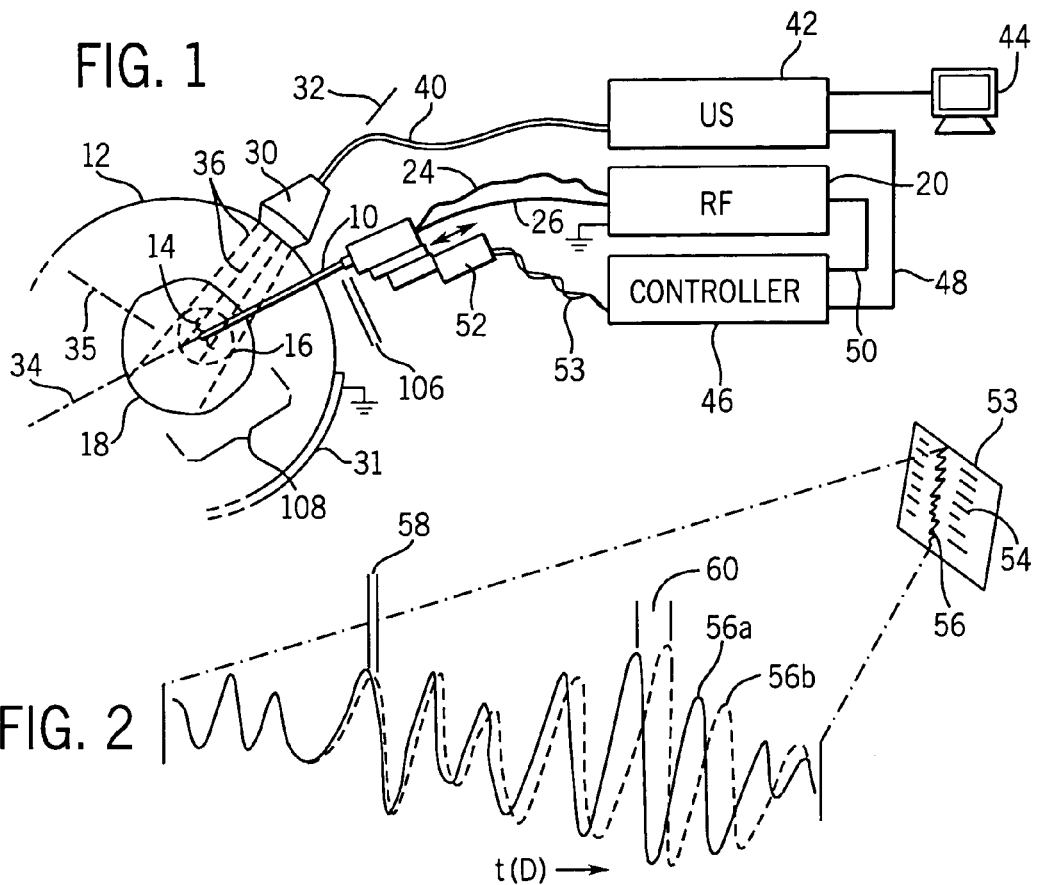
FIG. 1
FIG. 2
FIG. 3
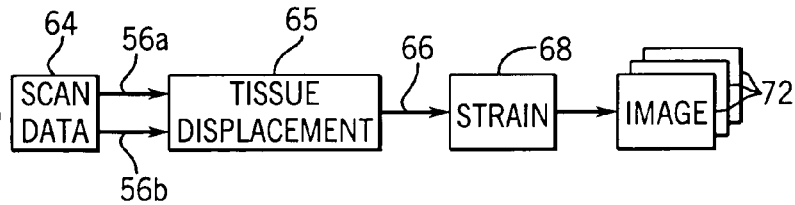
FIG. 4
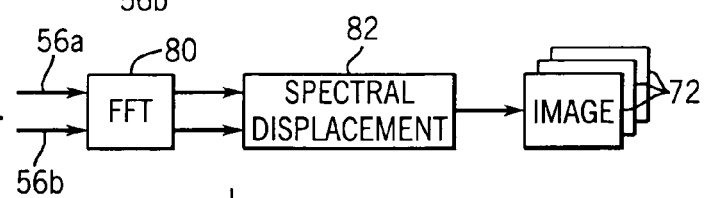
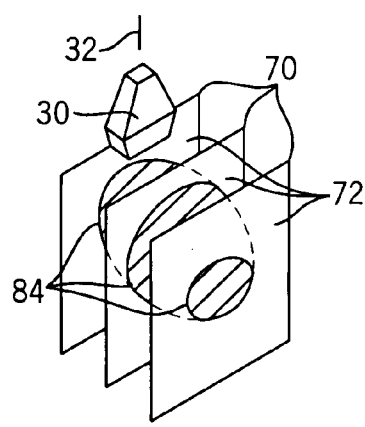
FIG. 5

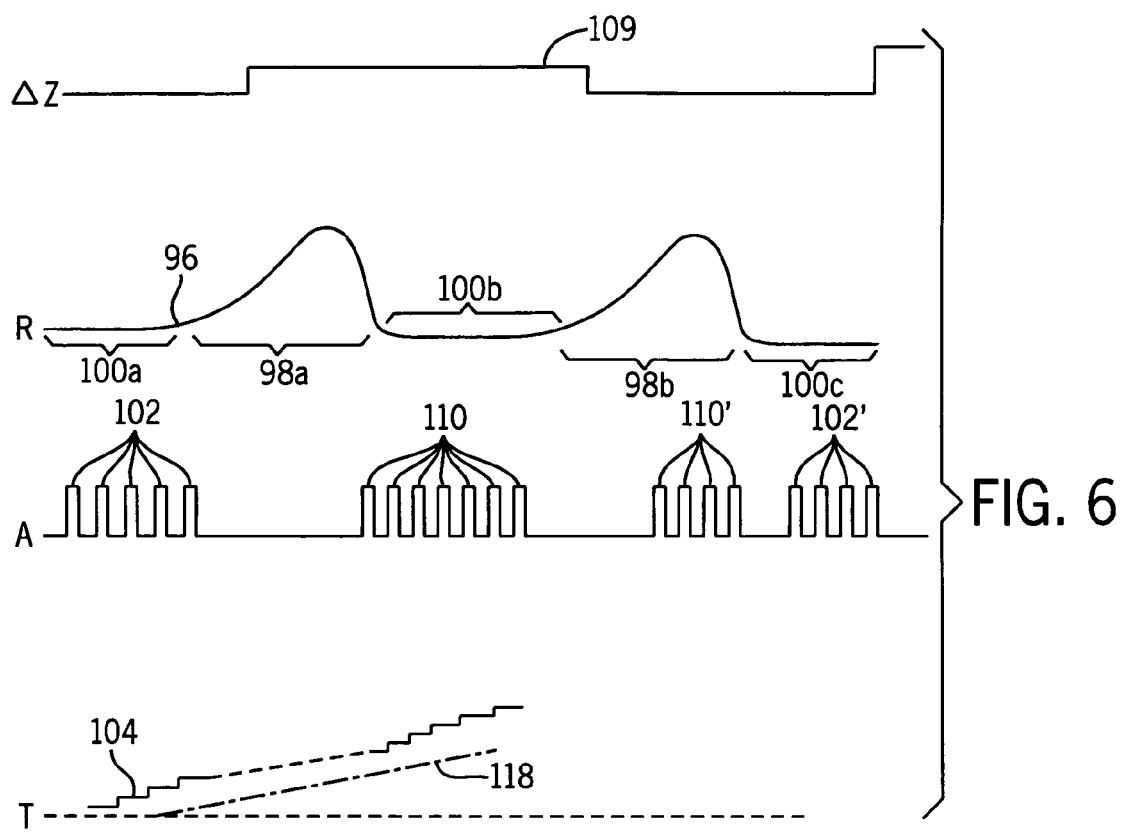
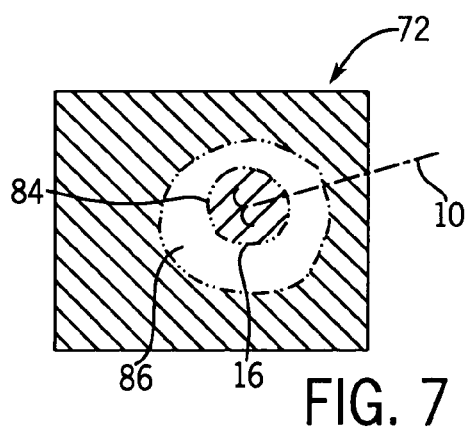
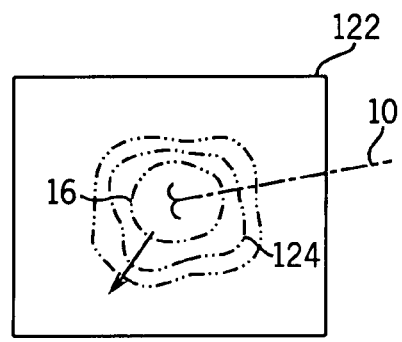
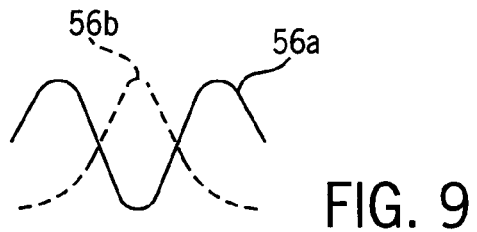
FIG. 6
FIG. 7
FIG. 8
FIG. 9

ELASTOGRAPHIC IMAGING OF IN VIVO SOFT TISSUE

CROSS-REFERENCE TO RELATED APPLICATIONS

--

STATEMENT REGARDING FEDERALLY SPONSORED RESEARCH OR DEVELOPMENT

--

BACKGROUND OF THE INVENTION

The present invention relates to medical imaging, and in particular to methods of in vivo elastographic imaging.

Elastography is a new imaging modality that reveals the stiffness properties of tissues, for example, axial strain, lateral strain, Poisson's Ratio, Young's Modulus or other common stiffness measurements. The measurements provide a two-dimensional array of data in which array location corresponding to tissue locations in an image plane. The array of data may be mapped to a gray scale to form a picture.

In "quasi-static" elastography, two images of the tissue are obtained. The first image forms a base line of the tissue in an unstressed or relaxed state or under a small pre-compression. The second image is obtained with the tissue under compression. Displacement of the tissue between the two images is used to deduce the stiffness of the tissue. The quasi-static elastogram is analogous to a physician's palpation of tissue in which the physician determines stiffness by pressing the tissue and detecting the amount that the tissue yields under pressure.

In "dynamic" elastography, a low frequency vibration is applied to the tissue and the velocity of the resulting elastic waves is measured, for example, using ultrasonic Doppler detection. Elastography of both types may be conducted using imaging techniques other than ultrasound, including computed tomography (CT) and magnetic resonance imaging (MRI).

While elastography has great promise, in vivo elastography of soft tissue structures such as the liver and other abdominal organs can be difficult because externally applied axial compression may induce nonaxial or lateral slippage of the organ. This lateral motion can obscure true axial tissue compression used to deduce stiffness of the tissue.

SUMMARY OF THE INVENTION

The present inventors have recognized that compression of the tissue may be done by a probe inserted percutaneously into the tissue to be measured. The probe applies compression in a localized and controlled fashion and may stabilize the tissue against lateral slippage.

In one embodiment, the probe may be a radio frequency (RF) ablation electrode used for the ablation of soft tissue. The ablation lesion creates a zone of necrosis with greater stiffness than the surrounding tissue.

While the invention is applicable to a wide variety of imaging modalities, it is well suited for ultrasound imaging commonly used for probe guidance, for example, during RF ablation. Ultrasound imaging is sensitive to the temperature of the tissue as may change the speed of sound used for the imaging. Accordingly, the inventors have also developed a method of compensating ultrasound images for heating during the ablation process and/or of providing a separate thermographic image of the tissue during RF or other methods of ablation.

The invention makes possible three-dimensional elastography of in vivo tissues by collecting elastographic images of adjacent image planes. In the case of RF ablation, this three-dimensional data allows for computation of lesion volume size and position within the treated region.

Specifically then, one embodiment of the present invention provides a method of monitoring RF ablation of tissue and includes the steps of inserting an ablation electrode into an ablation region of the tissue and applying RF ablation current to the ablation region. The tissue may be subject to dynamic or quasi-static compression to obtain an elastogram demarcating the lesion formed by the RF ablation.

It is thus one object of the invention to provide a simple and effective method of monitoring lesion size during or after an RF ablation.

The compression of the tissue may be performed by the RF ablation probe.

It is an object of this embodiment of the invention to apply precise compression to the region of interest, in vivo, with minimal lateral slippage. The probe provides a concentrated compressive force undiffused by intervening tissue and serves to stabilize the region while it is compressed.

The invention may include monitoring periodic physiological motion and acquiring a compression and baseline image, compared to produce the elastogram, in a period of minimal periodic physiological motion such as breathing or the like.

Thus, it is the object of one embodiment of the invention to minimize other sources of tissue movement when external or probe compression is applied.

Alternatively, the monitoring of the period physiological motion may be used to time the acquisition of the compression image at maximum compression caused by the periodic physiological motion and the baseline image at a period of minimal compression caused by the period physiological motion.

An object of this embodiment of the invention is to image an RF ablation lesion using naturally occurring compression of the tissue.

The invention may include the step of obtaining measurements of temperature increases caused by the RF ablation.

It is an object of this embodiment of the invention, therefore, to provide the ability to correct the elastogram of the lesion for temperature effects and/or to produce a thermographic image of the lesion and the surrounding tissue.

The method may include the steps of obtaining multiple images of planes through the tissue to produce a three-dimensional image indicating elasticity of the tissue in the region.

Thus, it can be an object of some embodiments of the invention to provide an image that may be used for better visualization of a lesion and/or for the calculation of its volume and the like.

More generally, the invention relates to the use of a probe to apply compression to tissues for elastographic imaging even when ablation is not contemplated.

It thus can be an object of the invention to provide for elastographic imaging of structures such as organs that are otherwise not easily compressed using external compression.

The images may be obtained using ultrasonic imaging techniques applying ultrasonic energy propagating along an insonification axis, and the probe may compress the tissue along the insonification axis. Further, the probe may be inserted along the insonification axis.

Thus, it is another object of the invention to provide for controlled lateral motion of the imaged organ when directional imaging techniques such as ultrasound are used.

The present invention makes practical three-dimensional elastographic imaging of in vivo tissue in which multiple elastographic images are obtained for multiple adjacent planes. The results of these images may be assembled to display a three-dimensional representation of, for example, an RF ablation lesion, or used for other three-dimensional operations including volume or perimeter calculations.

Thus, it is another object of the invention to provide for three-dimensional imaging of soft tissue within a patient using elastography.

The foregoing objects and advantages may not apply to all embodiments of the inventions and are not intended to define the scope of the invention, for which purpose claims are provided. In the following description, reference is made to the accompanying drawings, which form a part hereof, and in which there is shown by way of illustration, a preferred embodiment of the invention. Such embodiment also does not define the scope of the invention and reference must be made therefore to the claims for this purpose.

BRIEF DESCRIPTION OF THE FIGURES

FIG. 1 is a simplified block diagram of an RF ablation system for use with the present invention showing insertion of an ablation probe into a tumor site of an in vivo organ, an ultrasonic imaging system for imaging of the organ and tumor site, and further showing a control system for applying controlled quasi static compression to the tumor site through the RF ablation probe;

FIG. 2 is a graphical representation of an ultrasonic waveform received by the ultrasonic imaging system of FIG. 1 such as forms a single line of a B-scan ultrasonic image, the waveform shown before and after compression and showing a shifting of the signal corresponding to tissue movement within the tissue under compression;

FIG. 3 is a block diagram of the processing of the scan data of FIG. 2 to deduce tissue stiffness using a time-domain analysis technique;

FIG. 4 is a figure similar to that of FIG. 3 using a frequency-domain analysis technique;

FIG. 5 is a perspective representation of an ablation lesion reconstructed from multiple elastographic images taken in several adjacent planes according to techniques of FIGS. 1–4 above;

FIG. 6 is a graph showing compression, respiration, acquisition of images, and temperature, each as a function of time and illustrating different ablation schedules according to the present invention;

FIG. 7 is a simplified elastographic image of a lesion according to the techniques of FIGS. 1–6;

FIG. 8 is a simplified thermographic image obtained as part of the ultrasonic elastogram;

FIG. 9 is a simplified representation of the process of deducing tissue movement per FIG. 3 showing the problem of decorrelation with rapid temperature rise;

DETAILED DESCRIPTION OF THE PREFERRED EMBODIMENT

Figure 10:
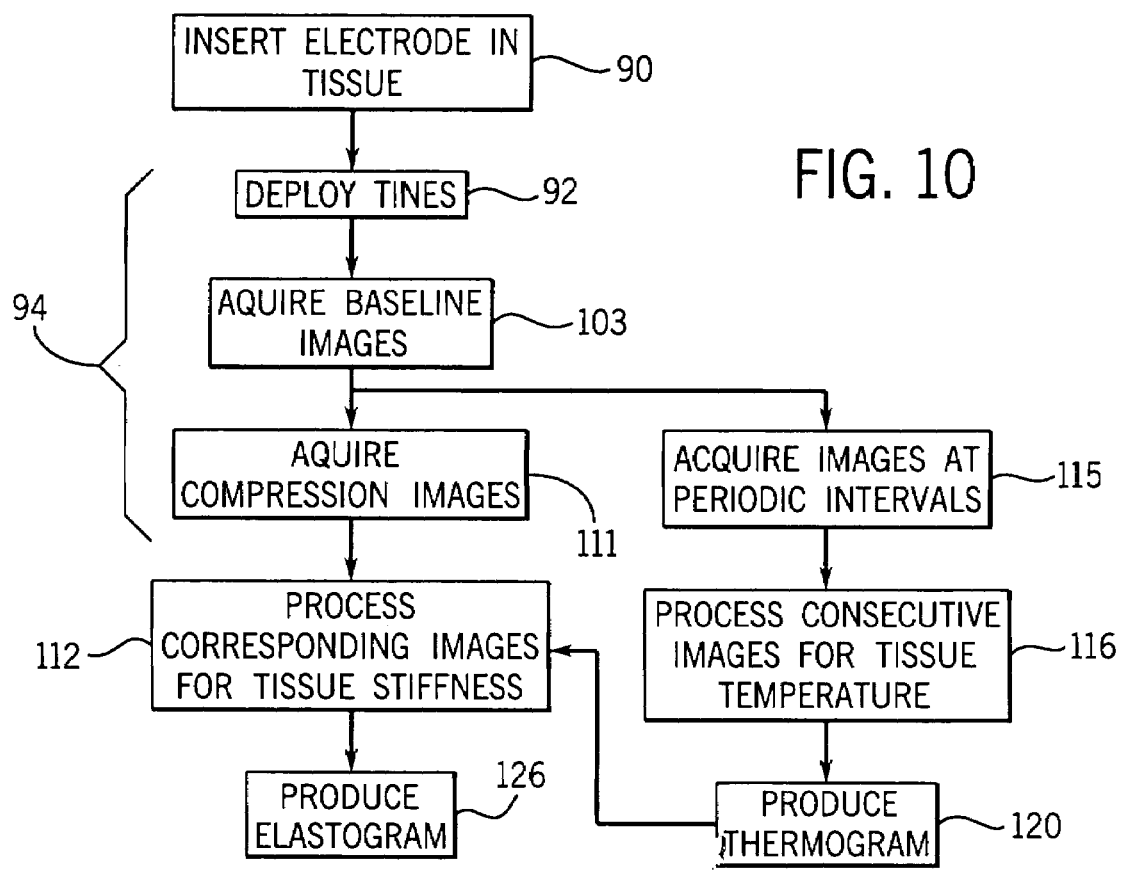
FIG. 10 is a flowchart showing the steps of producing the images of FIGS. 7 and 8.

Referring now to FIG. 1, an RF ablation probe 10 may be inserted percutaneously into a patient 12 to have its tip located at an ablation region 16 within an organ 18 such as the liver.

Extensible electrode tines 14, at the tip of the probe 10, may grip the tissue of the ablation region and provide a greater area of electrical contact to conduct ablative current from an RF source 20. Electrical energy from the RF source 20 is conducted through an insulated shaft of the probe 10 to the conductive tines 14 where ionic heating of the tissue kills tumor tissue. A large-area grounding pad 31 placed on the patient's skin provides a return path for this current. The tines 14 may include thermocouples for temperature measurements.

RF ablation probes 10 of this kind having extensible tines and thermocouple sensors are well known in the art and readily available. The RF 20 source may be a Rita Model 30 electrosurgical device manufactured by Rita Medical Systems Inc., Mountain View, Calif. or other similar device.

During the ablation process, electrical current is conducted from the RF source 20 along line 26 to the ablation probe 10. The temperature signal is returned along line 24 to be received by the RF source 20 and used to limit the temperature of ablation according to techniques well understood in the art.

Location of the probe 10 may be done using any ultrasonic imaging system, for example, the Acuson 128 XP Real Time Scanner manufactured by Acuson Incorporated of California. The ultrasonic imaging system includes an ultrasonic transducer 30 and ultrasonic processing electronics 42. The ultrasonic transducer 30 may be, for example, a linear array transducer approximately forty millimeters wide, operating with dynamic focus over a forty percent bandwidth and producing signals at a center frequency of five megahertz. Generally, 1 D, 1.5 D and 2 D transducers 30 are suitable for the image generating process.

During insertion of the probe 10, the ultrasound transducer 30 is placed against the skin of the patient and moved as needed for accurate visualization of the tip of the probe 10 with respect to the organ 18.

During the elastographic imaging to be described, the axis 32 of the ultrasound transducer 30 (along which the signals 36 propagate) is aligned as close as possible to the axis 34 along which the probe 10 is inserted and directed to send the ultrasonic signals 36 into the ablation region 16. The probe 10 stabilizes the organ 18 and prevents lateral shifting along axis 35.

During both procedures, each signal 36 travels into the tissue and is reflected at various tissue structures and boundaries. These echoes are detected by the ultrasound transducer 30 and conducted by cable 40 to the ultrasound processing circuitry 42. The received signals are digitized at a sampling rate of approximately 50 megahertz and then processed according to techniques well known in the art, to produce an image, for example, a B scan image, on display terminal 44. The signals 66 lie generally along a plane incorporating axis 34 and defining an image plane of the B-scan image.

According to the invention, the digitized echo signals may be further processed within the ultrasonic processing circuitry 42 to produce an elastographic image or may be transmitted to a separate controller 46 for processing there, as will be described. In the former case, line 48 communicates signals from the controller 48 to the ultrasonic processing circuitry 42 to coordinate generation of the elastographic image, in the latter case line 48 carries the control signals from the ultrasound system and digitized echo signals from the ultrasonic processing circuitry 42 to the controller 48 for processing by the controller 48.

The controller 46, which may be a computer or logic controller programmed, as described below, also receives temperature information via the RF source 20 along cable 50. This temperature information may also be used to provide control signals to the RF source 20 from the controller 48 to further control the RF ablation as well as to generate and normalize thermographic images as will be described. Controller 46 also provides output lines 53 connected to a motorized carriage 52, for example, one using a stepper motor and a lead screw to provide motion of the probe 10 along its insertion axis 34 in a controlled manner according to signals on output line 53 as will also be described. Other mechanisms for implementing the motorized carriage 52 may be used including those which apply a predetermined compressive force or low frequency oscillation. The controller 46 may also communicate with display terminal 44 for displaying images and receiving user input commands Referring now to FIG. 2, signals 36 may be preprocessed by the ultrasound processing circuitry 42 for focusing, noise rejection and the like to produce image signals 56. The varying amplitude of each image signal 56 is mapped to brightness of corresponding pixels 54 forming the columns of the B-scan image 53. Thus, each column of the image 53 is generated from what is essentially a time-domain signal 56 where the time axis also generally reflects distance from the ultrasound transducer 30 to the tissue feature shown in the image 53.

In quasi-static elastography, the stiffness of the tissue that is the subject of the image 53 may be determined by comparing two ultrasound echo-signal images 53 (made up of signals 56a and 56b, respectively) during different degrees of compression of the tissue. For example, as directed by signals from the controller 46, a first (baseline) signal 56a may be acquired of the ablation region 16 with the tissue uncompressed, or with a first degree of compression. Upon completion of this image acquisition, controller 46 causes an incremental inward movement of the probe 10 causing compression of the tissue of the ablation region 16 by the extended tines 14. A second (compression) signal 56b may then be acquired. This second signal 56b will generally exhibit an expansion in time reflecting a compression of the subject tissues away from the ultrasound transducer 30.

A general translation of tissue of the ablation region 16 would cause an equal offset between all the points of signals 56a and 56b over time (and hence over distance). However, the elasticity of the tissue causes tissue compression which in turn produces a gradient in the offset of the signals 56a and 56b as a function of time and distance. Generally, the difference 58 between signals 56a and 56b at early times and hence from tissue near the ultrasonic transducer 30 will be smaller than the separation 60 at later times and for tissue further away from the ultrasound transducer 30. The gradient of these displacements over the region of the ablation region 16 produces an elastogram of the tissue of the ablation region 16.

Referring to FIG. 3, ultrasonic scan data 64 from the ultrasound processing circuitry 42 (being complete image sets of signals 56a and 56b) are processed to determine tissue displacement along an axis from the ultrasound transducer 30 through the ablation region 16 by process block 65. This displacement may be determined by analyzing short segments of signals 56a and 56b and moving one segment with respect to the other until the best match is obtained. The amount of movement needed for the best match determines tissue displacement. The matching process may be implemented by means of mathematical correlation of the segments.

The displacement of the tissue, represented by displacement signal 66, is further processed by process block 68 which determines strain as the gradient of the displacement signal 66. The strain signal may be mapped to brightness values in elastographic images 72. Each of the process blocks may be implemented through a combination of hardware and software in controller 46 or ultrasound processing circuitry 42 according to well-known signal processing techniques.

Referring now to FIG. 7, the elastographic image 72 will provide for a high contrast region 84 showing a zone of tissue necrosis about the tines 14 such as causes a greater stiffness in that tissue. In this way, progress of the ablation may be tracked. Generally, a light band 86 may surround the necrotic tissue representing heated soft tissue, as will be described below, further improving the contrast of the image.

Referring now to FIG. 5, this process of generating an elastographic image 72 may be repeated with the ultrasound transducer 30 moved to different image planes 70 being parallel and adjacent to each other, or in a fan-like array of planes produced with a tipping of the ultrasonic transducer 30, or other pattern so as to cover an entire volume of the ablation region 16. These multiple planes 70 provide corresponding multiple elastographic images 72. The high contrast regions 84 of each of the elastographic images 72 may be assembled to define a three-dimensional volume of the actual lesion. Such a three-dimensional data set allows computation of lesion volume and lesion shape and may better indicate the location and orientation of the lesion.

Referring now to FIG. 4, alternative algorithms may be used to create the elastographic images 72. In one such algorithm, the signals 56a and 56b may be received by process block 80 to extract a spectra of the signals 56a and 56b using, for example, the well-known fast Fourier transform algorithm. The spectra of the signals 56a and 56b will be shifted according to the Fourier transformation property that causes dilation in a time-domain signal to produce a down-frequency shift in its frequency-domain spectrum. The amount of shift may be determined at process block 82 using correlation techniques similar to those used in process block 65 but executed on the frequency-domain signals.

The shift between the spectra taken of different segments of the time-domain signals 56a and 56b centered at increasing time delays, provides a gradient signal to produce elastographic images 72. While the results are similar to the technique of FIG. 3, this approach may have some advantages in terms of robustness against noise and the like.

Heating of the tissue of the ablation region 16 during ablation changes the sound speed in the tissue and causes thermal expansion. Both of these effects produce a shift in the signals 56a and 56b similar to that caused by tissue displacement. Accordingly, the present invention, particularly when used with ultrasonic imaging, may be used to deduce the temperature of the ablation region 16 and if desired, to correct the stiffness image for temperature effects and/or produce a thermograph of the tissue. Breathing and other physiological activity may cause additional compression of the tissue. These effects may be moderated by timing of the image acquisitions or may be used to augment or in lieu of the compression provided by the probe 10. A detailed description of such corrections and a more complex protocol for generating elastograms 72 will now be described.

Referring now to FIGS. 1 and 10, at a first step in the ablation protocol, indicated by process block 90, the probe 10 is inserted into the patient 12, as before, using ultrasound or other imaging techniques to locate the tines 14 in the ablation region 16. At process block 92, the tines 14 may be deployed to provide a gripping of the tissue aiding in the compression to follow.

At this time, the RF ablation may be performed and completed and a baseline and compression image (containing signals 56a and 56b, respectively) acquired and an elastogram calculated of the lesion so formed, with the option of additional RF ablation being continued (with the probe 10 remaining in place) and additional images 53 being taken. Alternatively, the RF ablation may be performed during the time that the images 53 are being obtained, as indicated by bracket 94, for real time representation of the ablation lesion's growth.

Referring now to FIG. 6, during the period of image acquisition, physiological motion such as respiration of the patient, may be monitored, to time the acquisition of images 56 during periods when no additional compression is being applied to the tissue such as may alter the derived elasticity. In this regard, a respiration signal 96 may be obtained using a standard chest cuff or the like as is known in the field of magnetic resonance imaging. The respiration signal 96 will exhibit periods 98 of high diaphragm movement and periods 100 of relative quiescence.

During a first quiescence period 100a, a series of acquisitions 102 of baseline images may be obtained as ablative current is conducted into the tissue and without compression (or with a baseline compression). These baseline acquisitions 102, indicated by process block 115 of FIG. 10) provide a measurement of changes in signals 56a (shown in FIG. 2) resulting not from compression, but from temperature effects. A temperature difference may be calculated by determining the apparent tissue displacement and applying a gradient of tissue displacement to a empirically defined function relating displacement gradient to temperature rise as indicated by subsequent process block 116. Generally, some of the acquisitions used for process blocks 103 and 111 may be shared with process block 115.

Thus, each acquisition 102 can be used to derive a step in temperature function 104 of corresponding tissue during the period 100a. When the period 98a (of high physiological motion) occurs or no later than the beginning of period 100a of low physiological motion, the probe 10 may be moved to compress the tissue as indicated by signal 109, using the motorized carriage 52. Referring momentarily to FIG. 2, the amount of movement 106 of the probe 10 may be limited to provide approximately 1% compression to the tissue with respect to the total organ size 108. In the preferred embodiment, incremental motion of one millimeter may be used.

During the next quiescent period 100b, acquisitions 110 may occur providing compression images 53 as indicated by process block 111 of FIG. 10. These compression acquisitions 110 may be compared to themselves to deduce changes in the temperature function 104 (per later process block 116) and compared to the baseline images 53 of acquisition 102 to deduce elasticity per later process block 112.

Referring still to FIG. 6, at period 100c, a new baseline acquisition 102' may be obtained and this process repeated with additional interleaved baseline and compressive acquisitions occurring. These later compressive acquisitions may use increased compression, for example, by moving the probe 10 an additional increment up to a compression limit at which time the probe 10 may be retracted to its initial position.

Referring now to FIG. 9, during the period 98a, when no acquisitions occur, there may be substantial displacement of the signals 56a and 56b caused by temperature effects. It will be understood that beyond a certain displacement of signals 56a and 56b correlation will be lost because there may be multiple local maxima in the correlation, each of which represents a plausible amount of heating or tissue deformation. Accordingly, the amount of temperature change during period 98a is generally not known. To remedy this, at process block 116, an extrapolation of the rate of temperature increase in period 98a may be used as a starting point for measured temperature increases in period 100b. Alternatively, the change in the temperature signal 104 from the thermocouple in the probe 10 may be used to estimate the change in temperature during period 98a.

Figure 11:
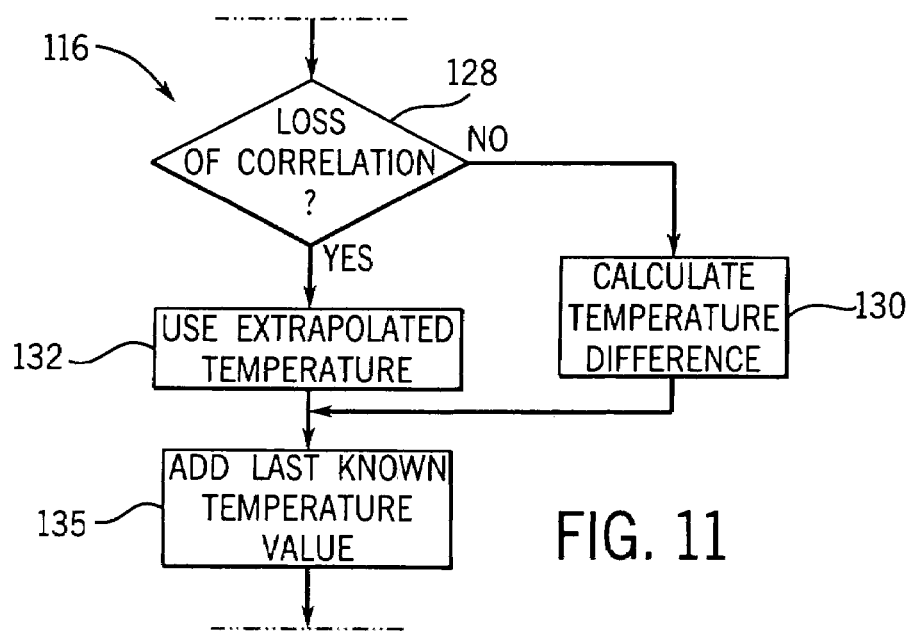
FIG. 11 is a detailed flowchart showing the calculation of temperature over periods of possible decorrelation per FIG. 9.

Referring now to FIG. 11, within process block 116, at a decision block 128, it is determined whether correlation is likely lost because of a lapse in time. If not, a new change in temperature is calculated for each pixel, at process block 130, based on the apparent tissue displacement of the corresponding portions of signals 56a or 56b. This change in temperature is added to the last known temperature for those pixels at process block 135.

If correlation is likely lost as determined by process block 128, then as indicated by process block 132, an extrapolated temperature is determined by looking at the rate of historical temperature increase (during period 100a) and or the rate of temperature increase for one pixel indicated by the thermocouple through probe temperature signal 118. This change in temperature is added to the last known temperature for those pixels at process block 135.

While only a single temperature signal 104 is shown, it will be understood that the invention in fact provides a temperature value for the tissue corresponding to each pixel of the images 53 in the same way that elasticity data is provided for each such pixel.

Referring again to FIG. 10, at process block 120, a thermal image 122 (shown in FIG. 8) may be generated from this temperature data such as will generally show an increasing region 124 of elevated temperature expanding about the ablation region 16. As indicated by FIG. 10, the temperature information may be used to modify the elasticity information received at process block 112 by subtracting an inferred temperature effect (i.e., the expected shift in the signals 56a and 56b expected from the measured temperature increase and the resultant thermal expansion). For this purpose, the relationship of temperature to offset of signals 56a and 56b need not be known precisely because conversion to absolute temperature need not be performed.

At process block 126, corrected elastographic images 72 are produced. The process of process block 126 may be repeated to obtain three-dimensional data and outputs of volume, diameter and the like may be provided.

Referring again to FIG. 6, in an alternative embodiment, the acquisition 110' of compression images may be performed during period 98b of maximum physiological motion eliminating the need for compression by the RF probe and useful in situations where imaging is to be obtained without ablation. This motion of the diaphragm can be used to generate stiffness or strain images. This is done by obtaining a baseline ultrasound echo-signal frame, followed by the post-compression ultrasound echo-signal frame after a specified time-interval.

Temperature imaging in the absence of physiological motion or other motion artifacts is performed by obtaining a baseline ultrasound echo-signal image and subsequent ultrasound echo-signal images obtained at periodic intervals. Temperature maps display the initial temperature rise and are continuously updated over time. The periodic acquisition of data has to be at a sufficient frame rate to avoid loss of correlation between consecutive frames. We have used a frame rate of 2 frames/sec using the 5 MHz transducer. However, higher frames rates are required for higher frequency transducers and faster rates of temperature increases.

It will be understood that the techniques described herein are examples that fall within the claims and that a number of variations are possible. For example, although ultrasound imaging is useful for probe location and commonly used, the techniques described herein may be applied to CT, MRI and other image techniques that provide indication of tissue movement. The technique of compressing tissues with a probe need not include RF ablation and the probe 10 need not be the compressive force when imaging a lesion formed by RF ablation. When a probe is used for compression, it need not be an RF ablation probe, but for example may without limitation include microwave ablation probes, laproscopic probes, other percutaneous probes or other internally inserted compression devices. The present invention is not limited to quasi-static compressions, but can be used with low frequency vibration compressions of a single frequency or chord of frequencies introduced through the probe 10 in which case Doppler readings of shear waves may be obtained from the ultrasound device. Low frequency vibration may also be used in the present invention to generate MRI elastograms by developing data over k-space. Generally, the tines 14 need not be extended from the probe 10 after the lesion has begun and may be optional if sufficient friction exists between the probe 10 and tissue. The elastogram may also be used to visualize the tumor before RF ablation.

It is specifically intended that the present invention not be limited to the embodiments and illustrations contained herein, but that modified forms of those embodiments including portions of the embodiments and combinations of elements of different embodiments also be included as come within the scope of the following claims.

We claim:

1. A method of monitoring destruction of tumorous tissue by RF electrical ablation comprising the steps of:
   (a) inserting an ablation electrode into an ablation region of the tissue and applying an RF ablation current to the ablation region, the electrode having a shaft and a tip, the tip locatable at the ablation region by piercing the tissue of the ablation region;
   (b) obtaining a baseline image of the region indicating tissue location;
   (c) applying compression to the region by manipulation of a portion of the shaft of the probe outside of the tissue to cause motion of the tip in the ablation region;
   (d) using the compression applied by the tip of the probe to obtain a compression image of the region indicating new tissue locations; and
   (e) comparing the baseline and compression images to determine displacement of tissue locations between the baseline and compression images;
   (f) determining a gradient of the displacement of tissue locations to obtain an image indicating elasticity of the tissue in the region such as may demarcate the lesion formed by the RF ablation.

2. The method of claim 1 wherein the compression is along the axis of insertion of the ablation electrode and wherein the ablation electrode is substantially inflexible in use to reduce shifting of the tissue perpendicularly to the compression and axis of insertion.

3. The method of claim 1 including the step of repeating steps (b) through (f) and reapplying the RF current after repetitions of step (d) to track the progress of the lesion during ablation.

4. The method of claim 1 wherein the images are obtained using ultrasonic imaging techniques and including the steps repeating at least one of steps (b) and (d) at periodic intervals to obtain a measurement of temperature increases in the tissue caused by the RF ablation concurrently with the image indicating elasticity, the temperature deduced from apparent displacement of the tissue without compression.

5. The method of claim 4 including at step (e) correcting at least one of the images by inferred speed of sound changes caused by changes in tissue temperature.

6. The method of claim 4 further including the step of displaying an: image of temperatures concurrently with the image indicating elasticity.

7. The method of claim 1 including the step of monitoring periodic physiological motion and wherein steps (c) and (d) are timed to occur in periods of minimal periodic physiological motion.

8. The method of claim 1 including the step of monitoring periodic physiological motion and wherein step (b) is timed to occur in periods of low compression caused by the periodic physiological motion and (d) are timed to occur in periods of high compression caused by the periodic physiological motion.

9. The method of claim 1 including the steps of repeating steps (c) and (d) to obtain images of adjacent planes through the tissue to produce a three-dimensional image indicating elasticity of the tissue in the region.

10. The method of claim 9 wherein the adjacent planes are selected from the group consisting of: parallel planes obtained by translating an ultrasonic transducer and fan-arrayed planes obtained by tilting an ultrasonic transducer at small angles.

11. The method of claim 10 wherein the ultrasonic transducer is selected from the group consisting of: 1D, 1.5D and 2D transducers.

12. The method of claim 1 wherein the ablation region is within an in vivo organ.

13. The method of claim 1 wherein the base line and compression images are obtained using an image modality selected from the group consisting of: computed tomography imaging, magnetic resonance imaging, and ultrasonic imaging.

14. The method of claim 1 wherein the images are obtained using ultrasonic imaging techniques applying ultrasonic energy propagating along an insonification axis and wherein the ablation electrode compresses the tissue along the insonification axis.

15. The method of claim 1 wherein the determination of elasticity includes the step of computing the gradient in tissue movement, where tissue movement is measured within the region by finding the maximum correlation in corresponding first and second portions of the baseline and compression images as a function of displacement of one portion with respect to the other.

16. The method of claim 1 wherein the determination of displacement of tissue includes the step of determining the maximum correlation in—the spectra of the baseline and compression images as a function of displacement of one spectrum with respect to the other.

17. The method of claim 1 wherein the ablation electrode includes extensible electrodes further piercing the ablation region to grip the ablation region after insertion.

18. The method of claim 1 wherein the step of applying compression includes using a compression fixture attached to the ablation electrode, wherein the compression fixture moves the ablation electrode along the axis of insertion by a predetermined amount.

19. The method of claim 18 wherein the predetermined amount is substantially less than 2% of the length of ablation region being imaged.

20. The method of claim 18 wherein the compression fixture includes an electronic actuator.

21. The method of claim 18 further including a controller communicating with the compression fixture and an ultrasonic imaging system and including the step of obtaining ultrasonic images before and after compression using the compression fixture.

22. The method of claim 1 including the step of calculating a volume of the lesion.

23. A method of monitoring RF ablation of tissue comprising the steps of:
   (a) inserting an ablation electrode into an ablation region of the tissue;
   (b) applying an RF ablation current to the ablation region;
   (c) obtaining ultrasound images of the region at periodic intervals indicating apparent tissue locations; and
   (d) processing the images to obtain displacement images
   (e) accumulating displacement from the displacement images/
   (f) taking the gradient of the accumulated displacements at specified times to obtain images indicating temperature of the tissue in the region such as may demarcate the lesion formed by the RF ablation.

* * * * *

UNITED STATES PATENT AND TRADEMARK OFFICE
CERTIFICATE OF CORRECTION

| | | |
|---|---|---|
| PATENT NO. | : 7,166,075 B2 | Page 1 of 1 |
| APPLICATION NO. | : 10/094844 | |
| DATED | : January 23, 2007 | |
| INVENTOR(S) | : Tomy Varghese et al. | |

It is certified that error appears in the above-identified patent and that said Letters Patent is hereby corrected as shown below:

IN THE SPECIFICATION

Col. 1, line 12: Delete "--" and substitute: --This invention was made with United States government support awarded by the following agency: NIH CA39224. The United States government has certain rights in this invention.--

Signed and Sealed this

First Day of December, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,166,075 B2 | Page 1 of 1 |
| APPLICATION NO. | : 10/094844 | |
| DATED | : January 23, 2007 | |
| INVENTOR(S) | : Tomy Varghese et al. | |

It is certified that error appears in the above-identified patent and that said Letters Patent is hereby corrected as shown below:

In the Specification

<u>Column 1, Lines 9-12:</u>
Delete the phrase:
"STATEMENT REGARDING FEDERALLY SPONSORED RESEARCH OR DEVELOPMENT --"

And replace with:
--REFERENCE TO GOVERNMENT RIGHTS
This invention was made with government support under CA039224 awarded by the
National Institutes of Health. The government has certain rights in the invention.--.

This certificate supersedes the Certificate of Correction issued December 1, 2009.

Signed and Sealed this
First Day of December, 2020

Andrei Iancu
*Director of the United States Patent and Trademark Office*